United States Patent [19]

Shaffer et al.

[11] Patent Number: 5,087,631
[45] Date of Patent: Feb. 11, 1992

[54] OXATHI(SIV)AZOL-5-ONE COMPOUNDS

[75] Inventors: Joel E. Shaffer, Chapel Hill; Stephen A. Thomson, Durham, both of N.C.

[73] Assignee: Glaxo Inc., Research Triangle Park, N.C.

[21] Appl. No.: 629,936

[22] Filed: Dec. 18, 1990

[51] Int. Cl.$^5$ ............ C07D 291/04; A61K 31/41
[52] U.S. Cl. .................. 514/342; 514/360; 546/280; 548/122
[58] Field of Search .......... 548/122; 546/280; 514/342, 360

[56] References Cited

PUBLICATIONS

J. Pharm. Pharmasol., J. R. Parratt, 31, 801 (1979).
Pharm. Res., L. J. Ignarro, 6, 651 (1989).
Annu. Rev. Physiol., K. E. Kamm, et al., 51, 299 (1989).
Liebigs Ann. Chem., H. Gotthardt, et al., 1025 (1981).
Chem. Ber., H. Gotthardt, 105, 188 (1972).
Tetrahedron Letters, H. Gotthardt, No. 17, 1277 (1971).
J. Am. Chem. Soc., A. Holm, et al., 97, No. 21, 6197 (1975).
Tetrahedron, A. Holm, 32, 2559 (1976).

*Primary Examiner*—Robert Gerstl
*Attorney, Agent, or Firm*—Charles T. Joyner

[57] ABSTRACT

The present invention relates to the compounds of formula (I).

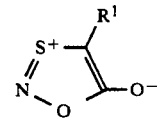

wherein $R^1$ is $C_{1-8}$ alkyl, $C_{2-8}$ alkenyl, $C_{5-8}$ cycloalkyl, aryl-$C_{1-4}$ alkyl, aryl or heteroaryl; or aryl or heteroaryl which is mono-, di-, or trisubstituted independently with halogen, nitro, $C_{1-4}$ alkyl, $C_{1-4}$ alkoxy, trifluoromethyl, amino or $C_{1-4}$ alkyl mono or disubstituted amino, pharmaceutical formulations containing these compounds and their use as vasodilators in the treatment of cardiovascular disorders.

12 Claims, No Drawings

OXATHI(SIV)AZOL-5-ONE COMPOUNDS

The present invention relates to 4-substituted 5H-1,3,2-oxathi(SIV)azol-5-ones (also known as 4-substituted 1,3,2-oxathiazolium-5-oxides) and the use of these compounds in the treatment of cardiovascular disorders.

BACKGROUND OF THE INVENTION

Since the discovery of the vasoactive effects of glyceryl trinitrate (also referred to as nitroglycerin), compounds containing nitrate or nitrite esters groups have been used in the treatment of various cardiovascular disorders such as, angina pectoris, congestive heart failure and myocardial infarction. See Parratt, J. R., *J. Pharm. Pharmacol.*, 31, 801 (1979). The utility of these compounds arises from their ability to release nitric oxide (NO). See Ignarro, L. J., *Pharmacology and Pharmaceut. Res.*, 6, 651 (1989). NO is believed to activate a soluble form of guanylate cyclase, a cellular enzyme, which catalyses the formation of 3',5' cyclic guanosine monophosphate (cGMP). See Kamm, et al., *Annu. Rev. Physiol.*, 51, 299 (1989). It is the action of cGMP on other cellular targets that is thought to mediate relaxation of vascular smooth muscle and provide the therapeutic effect of nitrovasodilators.

SUMMARY OF THE INVENTION

We have now found that certain 4-substituted 5H-1,3,2-oxathi(SIV)azol-5-ones of formula (I) below, are potent smooth muscle relaxants, promoters of increased intracellular levels of cGMP and vasodilators.

The present invention relates to the compounds of formula (I),

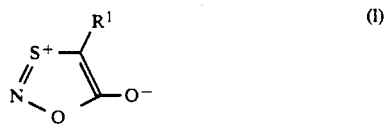

(I)

wherein $R^1$ is $C_{1-8}$ alkyl, $C_{2-8}$ alkenyl, $C_{5-8}$ cycloalkyl, aryl-$C_{1-4}$ alkyl, aryl or heteroaryl; or aryl or heteroaryl which is mono-, di-, or trisubstituted independently with halogen, nitro, $C_{1-4}$ alkyl, $C_{1-4}$ alkoxy, trifluoromethyl, amino or $C_{1-4}$ alkyl mono or disubstituted amino, pharmaceutical formulations containing these compounds and their use as vasodilators in the treatment of cardiovascular disorders.

Particular compounds of formula (I) are those wherein $R^1$ is phenyl or phenyl substituted with a halogen, nitro, $C_{1-4}$ alkyl or $C_{1-4}$ alkoxy function. Specific compounds of formula (I) are:
4-(4-methoxyphenyl)-5H-1,3,2-oxathi(SIV)azol-5-one,
4-phenyl-5H-1,3,2-oxathi(SIV)azol-5-one,
4-(4-nitrophenyl)-5H-1,3,2-oxathi(SIV)azol-5-one and
4-methyl-5H-1,3,2-oxathi(SIV)azol-5-one.

Those skilled in the art will recognize that compounds of formula (I) can be depicted in more than one resonance form, i.e.

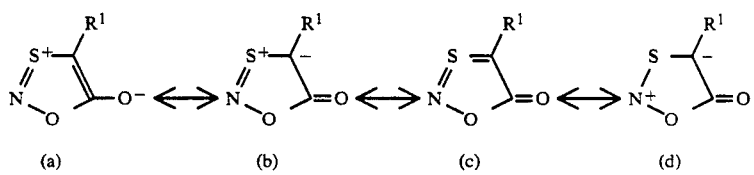

(a)  (b)  (c)  (d)

For simplicity herein, form (a) is taken to represent all such resonance forms.

DETAILED DESCRIPTION OF THE INVENTION

In particular for the compound of Formula (I) $R^1$ is $C_{1-8}$ alkyl, e.g., methyl, butyl and octyl; $C_{2-8}$ alkenyl, e.g., $-CH_2-CH=CH_2$ and $-(CH_2)_2CH=CHCH_3$; $C_{5-8}$ cycloalkyl, e.g., cyclopentyl and cyclohexyl; aryl-$C_{1-4}$ alkyl, e.g., benzyl; aryl, e.g., phenyl or naphthyl; heteroaryl, e.g. a 5, 6 or 7 member ring interrupted by one or more N, S or O hetero atoms, such as pyrrolyl, imidazolyl, furyl, thienyl, pyridazinyl, pyridyl, pyrimidinyl and pyrazinyl (preferably no two O or S atoms are adjacent in said heteroaryl) or such aryl (preferably phenyl) or heteroaryl bearing 1 to 3 substituents independently selected from halogen (e.g. chloro or bromo), nitro, $C_{1-4}$ alkyl (e.g., methyl, ethyl, propyl and butyl); $C_{1-4}$ alkoxy (e.g. methoxy, ethoxy, propoxy and butoxy), trifluoromethyl, amino, $C_{1-4}$ alkyl mono- or disubstituted amino (e.g., $-NHCH_3$, $-NHCH_2CH_3$ and $-N(CH_3)_2$).

The compounds of formula (I) may be prepared by methods known in the art of organic synthesis, an example being shown in Scheme 1:

SCHEME 1.

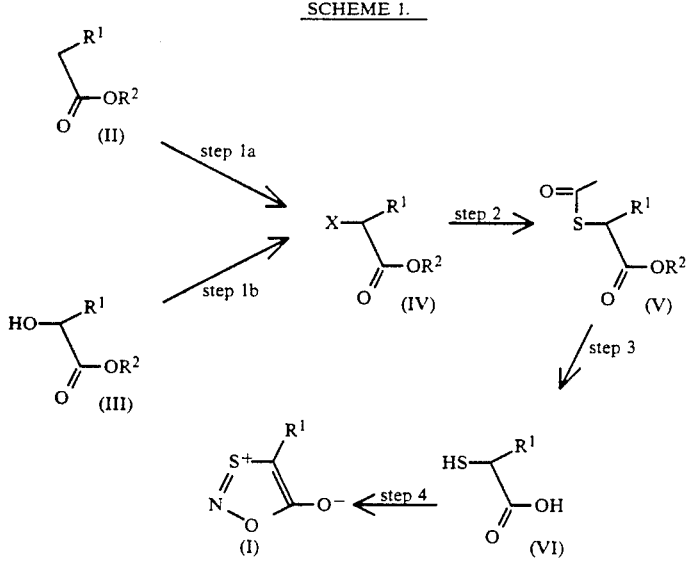

In step 1a, a substituted acetic acid or ester thereof of formula (II), wherein $R^1$ is as defined for formula (I) and $R^2$ is hydrogen; $C_{1-4}$ alkyl; benzyl or $-(CH_2)_n-Si(CH_3)_3$, wherein n is 1 to 5, can be converted to the corresponding compounds of formula (IV), wherein X is halogen, by treatment with a phosphorous trihalide in an aprotic solvent, e.g., a chlorinated hydrocarbon, for example, chloroform or methylene chloride; a dialkyl ether, for example, diethyl ether, or cyclic alkylene ether, for example, tetrahydrofuran, at a temperature of about 5° C. to about 100° C. Alternatively, a substituted mandelic acid or ester thereof of formula (III) wherein $R^1$ and $R^2$ are as defined above, can be converted to the corresponding compounds of formula (IV) by similar treatment. For example, a compound of formula (II) or (III) may be treated with $PBr_3$ in methylene chloride under reflux (about 40° C.) to yield a compound of formula (IV).

In step 2, a compound of Formula (IV) is reacted with an alkali metal thioacetate, e.g., sodium or potassium thioacetate, in a polar solvent, e.g., an alcohol, for example, ethanol, at a temperature of about 10° C. to about 100° C. to yield a compound of formula (V). For example, this step may be carried out by reacting a compound of formula (IV) with potassium thioacetate in ethanol under reflux (about 80° C.).

In step 3, a compound of formula (V) is treated with a base, e.g., an alkali hydroxide, for example, sodium or potassium hydroxide, in a mixture of a protic solvent and water, e.g., a mono or polyhydroxy alcohol and water, for example ethanol or ethylene glycol and water, at a temperature of about 50° C. to about 130° C. to give a compound of formula (VI). For example, a compound of formula (VI) may be obtained by treating a compound of formula (V) with sodium hydroxide in a 50:50 ethanol water mixture under reflux (about 80° C.).

In step 4, a compound of formula (VI) is reacted with a $C_{(1-4)}$ alkyl nitrite, e.g., t-butyl nitrite, in an aprotic solvent, e.g., a chlorinated hydrocarbon, for example, chloroform or methylene chloride; a dialkyl ether, for example, diethyl ether, or cyclic alkylene ether, for example, tetrahydrofuran, followed by treatment with a dehydrating agent, e.g., a dialkylcarbodiimide, for example, dicyclohexylcarbodiimide, in the same or similar aprotic solvent, e.g., in the range of about 10° C. to about 80° C. to give a compound of formula (I). For example, this step may be carried out by reacting a compound of formula (VI) with dicyclohexylcarbodiimide in methylene chloride under reflux (about 40° C.).

Some compounds of formula (I) can be made through intraconversion from other compounds of formula (I). For example, the compound of formula (I) wherein $R^1$ is phenyl can be converted to a corresponding compound where $R^1$ is nitrophenyl, by nitration, e.g., treating with nitric and sulfuric acid at a temperature in the range of about $-15°$ C. to about 30° C. or to corresponding halophenyl compound by halogenation by any suitable methods in the art, e.g., treatment with N-bromosuccinimide in methyl chloride at a temperature in the range of about 20° C. to about 40° C.

The compounds of formula (I) may be used for the same disorders and administered by the same routes as the nitrovasodilators now in clinical use, i.e., glyceryl trinitrate and erythrityl tetranitrate. For example, chronic myocardial ischemia, congestive heart failure and angina pectoris, may be treated sublingually, orally, rectally, vaginally, transdermally, parenterally or by inhalation. Other conditions in which the compounds of formula (I) have utility include the treatment of Prinzmetal's angina, essential hypertension and pulmonary hypertension.

The amount of active compound, i.e., a compound of formula (I), required for treating the above conditions will vary with the particular compound chosen, the route of administration and the condition of the patient undergoing the treatment, and is ultimately at the discretion of the physician. However, a suitable oral, sublingual or inhalation dose for a mammal, including a human, is in the range of from about 0.01 mg to about 3.0 mg per kilogram body weight per day. For example, a typical dose for a human patient (about 60 to 80 Kg) is about 0.6 mg to about 240 mg per day; preferably 30 to 150 mg per day.

The desired daily oral, sublingual or inhalation dose is preferably presented as one to about six sub-doses administered at appropriate intervals throughout the day as needed. A sublingual sub-dose is preferably in the form of a tablet containing about 0.5 to 30 mg of active compound although other sublingual dosing media known in the art of pharmacy may be employed, e.g., sublingual aerosols. An oral sub-dose of about 0.5 to 30 mg of active compound may be in the form of a tablet, capsule, syrup, lozenge, suspension or other oral formulation known in the art. Multi-dose pressurized or dry powder dispensers are preferred for inhalation with each sub-dose being about 0.5 to about 30 mg of active compound.

The compounds of formula (I) may advantageously be administered transdermally to patients who require a small, but continuous dose. The total transdermal dose is about 0.1 to 3.0 mg/kg per day delivered at a uniform rate.

The compounds of formula (I) may be delivered by rectal or vaginal suppository. The total dose per day administered by this route is about 0.1 to 10.0 mg/kg.

Administration of the compounds of formula (I) may also be by a parenteral route such as injection or infusion. This route of administration is particularly useful when other routes are impractical. The infusion dose is about 0.001 to about 0.1 mg/kg per min, and the injection dose is about 0.01 to about 3.0 mg/kg per day given one to four injections per day.

Formulations of the present invention, for medical use, comprise an active compound together with a pharmaceutically acceptable carrier and optionally other therapeutically active ingredients. The carrier should be pharmaceutically acceptable in the sense of being compatible with the other ingredients of the formulation and not deleterious to the recipient thereof.

The present invention, therefore, further provides pharmaceutical formulations each comprising a compound of formula (I) together with a pharmaceutically acceptable carrier therefor.

The formulations include those suitable for oral (including sublingual), transdermal, buccal, nasal, vaginal, rectal or parenteral (including subcutaneous, intramuscular and intravenous) administration. Preferred routes of administration are oral and transdermal.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier and then, if necessary, shaping the product into desired unit dosage form.

Formulations for transdermal application may be prepared, for example, by mixing the active compound with a collodial silicone dioxide suspension and this suspension is sealed between two layers of polymeric laminate to form a thin "sandwich" transdermal system. The side which is in contact with the skin is made of a permeable polymer and its characteristics as a membrane control the release of the drug. The side facing away from the skin is a nonpermeable polymer. The permeable side is kept in contact with the skin by means of an adhesive or bandage.

Formulations of the present invention suitable for oral administration may be presented as discrete units such as capsules, cachets, tablets or lozenges, each containing a predetermined amount of the active compound; as a powder or granules; or a suspension in an aqueous liquid or non-aqueous liquid such as a syrup, an elixir, an emulsion or a draught.

A tablet may be made by compressing or molding the active compound, optionally with one or more accessory ingredients. Compressed tablets may be prepared by compressing in a suitable machine the active compound in a free-flowing form such as a powder or granules, optionally mixed with a binder, lubricant, inert diluent, surface active or dispersing agent.

For administration by inhalation or sublingual aerosol, the compounds of formula (I) are conveniently delivered in the form of an aerosol spray presentation from multi-dose pressurized packs, with a suitable propellant or, for inhalation, from a nebulizer. In the case of a pressurized aerosol, the dosage unit may be determined by a metering valve.

Alternatively, for administration by inhalation or insufflation, the compounds of formula (I) may take the form of a dry powder composition, e.g., a powder mixture of the compound of formula (I) an a suitable powder base e.g., lactose or starch. The powder composition may be presented in unit dosage.

A syrup may be made by adding the active compound to a concentrated, aqueous solution of a sugar, for example sucrose, to which may also be added any accessory ingredients. Such accessory ingredient(s) may include flavoring, an agent to retard crystallization of the sugar or an agent to increase the solubility of any other ingredient, such as a polyhydric alcohol for example glycerol or sorbitol.

Formulations for rectal or vaginal administration may be presented as a suppository with a conventional carrier such as cocoa butter or WITEPSOL S55 (trademark of Dynamit Nobel, Germany, for a suppository base of glyceryl esters of saturated fatty acids).

In addition to the aforementioned ingredients, the formulations of this invention may further include one or more optional ingredient(s) utilized in the art of pharmaceutical formulating, e.g. diluents, buffers, flavoring agents, binders, surface active agents, thickeners, lubricants, preservatives (including antioxidants) and the like.

EXAMPLES

The following examples illustrate aspects of this invention but should not be construed as limitations thereto. As used herein the symbols and conventions used in these examples are consistent with those used in the contemporary scientific literature, for example, the *Journal of the American Chemical Society*.

EXAMPLE 1

Aorta Vasodilation Assay

The thoracic aortas removed from euthanized male Sprague-Dawley rats (200-300 g) are cleaned of adherent connective tissue and cut into rings 3 to 5 mm in length. Endothelium is removed by rolling the rings on moist filter paper. Rings are suspended in an organ chamber containing a physiological salt solution of (mM): NaCl, 118.4; KCl, 4.7; $MgSO_4.H_2O$, 1.2; $CaCl_2.2H_2O$, 2.5; $KH_2PO_4$, 1.2; $NaHCO_3$, 25.0; and dextrose, 11.1. The bathing solution is maintained at 37° C. and half of the tissues are aerated with 95% $O_2$/5% $CO_2$ and half are aerated with 20% $O_2$/5% $CO_2$/75% $N_2$. Tissues are mounted to isometric force displacement transducers and responses are recorded on a polygraph.

All rings are gradually stretched (over a 120 min. period) to a basal resting tension of 2 g, which is maintained throughout the assay. During the basal tension adjustment period, the rings are exposed to KCl (40 mM) two to three times to verify tissue contractility. During this period, the effectiveness of endothelium removal is confirmed by the absence of the characteristic relaxation seen with acetylcholine ($1 \times 10^{-6}$M) in endothelium-intact (but not endothelium-removed) rings contracted with phenylephrine ($1 \times 10^{-7}$M).

Methylene blue ($1 \times 10^{-5}$M) is added to half of the tissues aerated at 20% $O_2$ and 95% $O_2$ to inhibit basal cGMP accumulation. Phenylephrine ($1 \times 10^{-7}$M) is then added and the rings are allowed to obtain a stable contractile response after which time, SOD (100 U/mL) is added to the tissues. The test compound is then added in a cumulative fashion. After the stabilization of the response to the last concentration of the test compound, sodium nitroprusside ($1 \times 10^{-4}$M) is added to induce complete relaxation. Table 1 shows the relaxation induced by each test compound expressed as $IC_{50}$ (20% $O_2$, without methylene blue condition).

TABLE 1

VASODILATION ASSAY

| Compound of Formula (I), $R^1$ = | $IC_{50}$ (µM) |
| --- | --- |
| 4-methoxyphenyl | 1.3 |
| phenyl | 2.3 |
| 4-nitrophenyl | 16 |
| methyl | 20 |

EXAMPLE 2

Pharmaceutical Formulations (A) Transdermal System

| Ingredients | Amount |
| --- | --- |
| Active compound | 25.0 mg |
| Silicone fluid | 450.0 mg |
| Colloidal silicone dioxide | 25.0 mg |

The silicone fluid and active compound are mixed together and the colloidal silicone dioxide is added to increase viscosity. The material is then dosed into a subsequently heat sealed polymeric laminate comprised of the following: polyester release liner, skin contact adhesive composed of silicone or acrylic polymers, a control membrane which is a polyolefin (e.g. polyethylene), polyvinyl acetate or polyurethane, and an impermeable backing membrane made of a polyester multilaminate. The system described is a 10 sq. cm patch.

(B) Sublingual Tablet

| Ingredients | Amount |
| --- | --- |
| Active compound | 5.0 mg |
| Starch | 10.0 mg |
| Magnesium Stearate | 1.0 mg |
| Sodium Saccharin | 10.0 mg |
| Flavoring agent | q.s. |

The active compound, starch, flavoring and sodium saccharin are granulated with water and dried. Magnesium stearate is added to the dried granules and the mixture is thoroughly blended. The blended mixture is compressed into a tablet.

(C) Sublingual Aerosol

| Ingredients | Amount |
| --- | --- |
| Active compound | 1.0 g |
| Propellant 12 ($Cl_2F_2C$) | 10.0 g |
| Oleic acid | 8.0 mg |
| Flavoring agent | q.s. |

A suspension is formed by mixing active compound with the propellant, oleic acid and flavor in a pressurized vessel equipped with internal mixing. Contents are charged into a metered dose dispenser using a pressure fill technique and then crimped. A metering valve is chosen so that each dose delivers substantially 5.0 mg of active compound.

(D) Oral Tablet

| Ingredients | Amount |
| --- | --- |
| Active compound | 5.0 mg |
| Starch | 20.0 mg |
| Magnesium Stearate | 1.0 mg |

The active compound and the starch are granulated with water and dried. Magnesium stearate is added to the dried granules and the mixture is thoroughly blended. The blended mixture is compressed into a tablet.

(E) Suppository

| Ingredients | Amount |
| --- | --- |
| Active compound | 25.0 mg |
| Theobromine sodium salicylate | 250.0 mg |
| Witepsol S55 | 1725.0 mg |

The inactive ingredients are mixed and melted. The active compound is then distributed in the molten mixture, poured into molds and allowed to cool.

EXAMPLE 3

4-(4-Methoxyphenyl)-5H-1,3,2-oxathi(SIV)azol-5-one (Formula (I), $R^1$=4-methoxyphenyl)

(A) 2-Trimethylsilylethyl 4-methoxymandelate (Formula (III), $R^1$=4-methoxyphenyl, $R^2$=$CH_2CH_2SiMe_3$)

To a solution of 4-methoxymandelic acid (2.00 g, 10.978 mmol) in 55 mL of dioxane at 90° C. is added 2-trimethylsilylethyl-N,N-diisopropyl-pseudourea. The resulting solution is refluxed for about 8 hours. After cooling the mixture is diluted with 50 mL of ethyl acetate, filtered, washed with saturated aqueous sodium bicarbonate followed by brine, dried over magnesium sulfate, and concentrated. The resulting residue is chromatographed on silica gel (9/1 hexanes/ethyl acetate) to give the title compound as an oil: 2.24 g, 72% yield. $^1$H NMR (300 MHz, CDCl$_3$): 7.32 (d, J=8.8, 2 H), 6.89 (d, J=8.8, 2 H), 5.08 (d, J=5.6, 1 H), 4.38-4.17 (m, 2 H), 3.81 (s, 3 H), 3.41 (d, J=5.6, 1 H), 0.96 (m, 2 H), 0.01 (s, 9 H).

(B) α-(4-methoxyphenyl)-α-bromoacetic acid trimethylsilylethyl ester (Formula (IV), $R^1$=4-methoxyphenyl, $R^2$=CH$_2$CH$_2$SiMe$_3$, X=Br)

To a solution of the compound of formula (III) ($R^1$=4-methoxyphenyl, $R^2$=CH$_2$CH$_2$SiMe$_3$, 1.98 g, 7.01 mmol) in 50 mL of chloroform is added a solution of PBr$_3$ in methylene chloride (1.00M in methylene chloride, 3.5 mL) dropwise. The reaction mixture was stirred at room temperature for about 45 minutes, then refluxed for about 45 minutes. The reaction mixture is then diluted with methylene chloride, washed with water, dried over magnesium sulfate and concentrated, to give the title compound as an oil: 2.05 g, 85% yield. $^1$H NMR (300 MHz, CDCl$_3$): 7.48 (d, J=8.8, 2 H), 6.88 (d, J=8.8, 2 H), 5.31 (s, 1 H), 4.38–4.15 (m, 2 H), 3.81 (s, 3 H), 1.02 (m, 2 H), 0.03 (s, 9 H).

(C) S-Acetyl-α-(4-methoxyphenyl)-α-mercaptoacetic acid trimethylsilylethyl ester (Formula (V), $R^1$=4-methoxyphenyl, $R^2$=CH$_2$CH$_2$SiMe$_3$)

To a solution of the compound of formula IV ($R^1$=4-methoxyphenyl, $R^2$=CH$_2$CH$_2$SiMe$_3$, X=Br, 2.20 g, 6.52 mmol) in 65 mL of anhydrous ethanol is added potassium thioacetate (930 mg, 8.14 mmol). The reaction mixture is stirred at room temperature for about 4.5 hours, concentrated to approximately 10 mL, diluted with 60 mL of brine, and extracted repeatedly with ethyl acetate. The combined organic phases are dried over magnesium sulfate, concentrated, and the residue chromatographed on silica gel (20/1 hexanes/ethyl acetate) to give the title compound as an oil; 1.90 g, 86% yield. $^1$H NMR (300 MHz, CDCl$_3$): 7.31 (d, J=8.8, 2 H), 6.86 (d, J=8.8, 2 H), 5.24 (s, 1 H), 4.37–4.16 (m, 2 H), 3.80 (s, 3 H), 2.35 (s, 3 H), 1.00 (m, 2 H), 0.01 (s, 9 H).

(D) α-(4-Methoxyphenyl)-α-mercaptoacetic acid (Formula (VI), $R^1$=4-methoxyphenyl)

To a solution of the compound of formula (V) ($R^1$=4-methoxyphenyl, $R^2$=CH$_2$CH$_2$SiMe$_3$, 1.00 g, 2.94 mmol) in 50 mL of ethanol is added 30 mL of 1N aqueous sodium hydroxide. The reaction mixture is flushed with nitrogen, stirred at room temperature for about 1.5 hours, then at 55° C. for about 3 hours. The resulting solution is concentrated to a volume of approximately 40 mL, diluted with 30 mL of water, washed with methylene chloride, acidified with concentrated hydrochloric acid, extracted with methylene chloride, dried over magnesium sulfate and concentrated to give the title compound as an off white solid: 530 mg, 91% yield. $^1$H NMR (300 MHz, CDCl$_3$): 7.36 (d, J=8.5, 2 H), 6.86 (d, J=8.5, 2 H), 4.66 (d, J=7.6, 1 H), 3.79 (s, 3 H), 2.58 (d, J=7.6, 1 H).

(E) 4-(4-methoxyphenyl)-5H-1,3,2-oxathi(SIV)azol-5-one (Formula (I), $R^1$=4-methoxyphenyl)

To a ice cold solution of the compound of formula (VI) ($R^1$=4-methoxyphenyl, 450 mg, 2.27 mmol), protected from the room lights, in 17 mL of methylene chloride is added tert-butyl nitrite (0.945 mL, 7.94 mmol), dropwise. The resulting red solution is stirred for about 20 minutes, then 1-(3-dimethylaminopropyl)-3-ethylcarbodiimide hydrochloride (870 mg, 4.54 mmol) is added. After stirring in an ice bath for about 1 hour, and at room temperature for about 2 hours, the mixture is washed with 1N aqueous hydrochloric acid, water, dried over magnesium sulfate, and concentrated. The resulting solid is crystallized from ethyl acetate/hexanes to give the title compound as an orange solid.; 310 mg, 69% yield, m.p.=110°–115° C. $^1$H NMR (300 MHz, CDCl$_3$): 7.81 (d, J=9.0, 2 H), 6.96 (d, J=9.0, 2 H), 3.85 (s, 3 H).

EXAMPLE 4

4-Phenyl-5H-1,3,2-oxathi(SIV)azol-5-one (Formula (I), $R^1$=phenyl) (A) S-Acetyl-α-phenyl-α-mercaptoacetic acid (Formula (V), $R^1$=phenyl, $R^2$=H)

To a solution of α-bromophenylacetic acid (2.00 g, 9.30 mmol), commericially available, e.g., Aldrich Chemical Co., Milwaukee, Wis., in 100 mL of anhydrous ethanol is added potassium thioacetate (2.125 g, 18.6 mmol), and the mixture is stirred for about 3 hours. The mixture is concentrated to approximately 10 mL, diluted with 50 mL of water, and washed with methylene chloride. The aqueous phase is acidified with concentrated hydrochloric acid, extracted with methylene chloride, dried over magnesium sulfate and concentrated to give the title compound as an off white solid: 1.940 g, 99% yield. $^1$H NMR (300 MHz, CDCl$_3$): 7.40–7.30 (m, 5 H), 5.31 (s, 1 H), 2.37 (s, 3 H).

(B) α-Phenyl-α-mercaptoacetic acid (Formula (VI), $R^1$=phenyl)

To an ice cold solution of ammonia in methanol (2.75M, 25 mL) is added the compound of formula (V) ($R^1$=phenyl, $R^2$=H, 1.940 g, 9.24 mmol) in 10 mL of methanol. The mixture is stirred at room temperature for about 1 hour, and then concentrated. The residue is dissolved in saturated sodium bicarbonate, washed repeatedly with ethyl acetate, acidified with concentrated hydrochloric acid, and extracted with ethyl acetate. The combined organics are dried over magnesium sulfate and concentrated to give the title compound an off white solid: 1.46 g, 94% yield. $^1$H NMR (300 MNz, CDCl$_3$): 7.48–7.30 (m, 5 H), 4.75 (d, J=9.7, 1 H) 2.62 (d, J=9.7, 1 H).

(C) 4-phenyl-5H-1,3,2-oxathi(SIV)azol-5-one (Formula (I), $R^1$=phenyl)

To an ice cold solution of the compound of (VI) ($R^1$=phenyl, 1.460 g, 8.69 mmol), from part (B), protected from room lights, in 75 mL of methylene chloride is added tert-butyl nitrite (1.5 mL, 12.6 mmol). After stirring for about 20 minutes the reaction mixture is diluted with 25 mL of methylene chloride, and dicyclohexylcarbodiimide (3.58 g, 17.35 mmol), in 20 mL of methylene chloride is added. The mixture is stirred in an ice bath for about 2 hours, filtered, concentrated, and the residue chromatographed on silica gel (4/1 hexanes-/ethyl acetate) to give the title compound as a yellow solid: 768 mg, 49% yield. M.P.=128°–130° C. $^1$H NMR (300 MHz, CDCl$_3$): 7.89–7.45 (m, 5 H), Anal. Calcd. for C$_8$H$_5$NO$_2$S: C, 53.62; H, 2.81; N, 7.82. Found: C, 53.47; H, 2.83; N, 7.80.

EXAMPLE 5

4-(4-nitrophenyl)-5H-1,3,2-oxathi(SIV)azol-5-one (Formula (I), $R^1$=4-nitrophenyl)

To about a −10° C. solution of the compound of formula (I) ($R^1$=phenyl, 100 mg, 0.56 mmol) from Example 4 in 1.5 mL of concentrated sulfuric acid is added concentrated nitric acid (0.050 mL, 0.78 mmol). After stirring while maintaining the temperature at about −10° C. temperature for about 2 hours the mixture is poured onto ice and extracted with chloroform. The combined organics are dried over sodium sulfate, concentrated, and the residue chromatographed on silica gel (4/1 hexanes ethyl acetate) to give ($R^1$=4-nitrophenyl) as a yellow solid: 75 mg, 60% yield. M.P.=143°-145° C. $^1$H NMR (300 MHz, CDCl$_3$): 8.34 (d, J=8.5, 2 H), 8.06 (d, J=8.5, 2 H). Anal Calcd. for $C_8H_4N_2O_4S$: C, 42.86; H, 1.80; N, 12.50. Found: C, 42.73; H, 1.98; N, 12.47.

EXAMPLE 6

4-Methyl-5H-1,3,2-oxathi(SIV)azol-5-one (Formula (I), $R^1$=CH$_3$)

To an ice cold solution of the compound of formula (VI) wherein $R^1$ is methyl, i.e., thiolactic acid (600 mg, 5.65 mmol), available form Aldrich Chemical Co., protected from room lights, in 7 mL of methylene chloride is added tert-butyl nitrite (0.40 mL, 7.07 mmol). After stirring for about 15 minutes, the mixture is diluted with 10 mL of methylene chloride, and dicyclohexylcarbodiimide (2.33 g, 11.06 mmol) in 7 mL of methylene chloride is added. After stirring in an ice bath for about 3.5 hours the mixture is filtered, concentrated, and the residue chromatographed on silica gel (2/1 hexanes/ethyl acetate) to give the title compound as a yellow solid 175 mg, 26% yield. $^1$H NMR (300 MHz, CDCl$_3$): 2.34 (s, 3 H). Anal. Calcd. for $C_3H_3NO_2S$: C, 30.76; H, 2.58 ; N, 11.96. Found: C, 30.82; H, 2.62; N, 11.92.

EXAMPLE 7

4-Cyclohexyl-5H-1,3,2-oxathi(SIV)azol-5-one (Formula (I), $R^1$=cyclohexyl)

This compound is prepared by the same procedure of Example 3 except that an equivalent amount of cyclohexylacetic acid ethyl ester, the compound of formula (II) where $R^1$ is cyclohexyl and $R^2$ is ethyl, is used in place of the compound of formula (III) where $R^1$ is 4-methoxyphenyl and $R^2$ is CH$_2$CH$_2$SiMe$_3$ in part (B).

EXAMPLE 8

4-(2-Pyridyl)-5H-1,3,2-oxathi(SIV)azol-5-one (Formula (I), $R^1$=2-pyridyl)

This compound is prepared by the same procedure of Example 3 except that an equivalent amount of 2-pyridylacetic acid, the compound of formula (II) where $R^1$ is 2-pyridyl and $R^2$ is hydrogen, is used in place of the compound of formula (III) where $R^1$ is 4-methoxyphenyl and $R^2$ is CH$_2$CH$_2$SiMe$_3$ in part (B).

EXAMPLE 9

4-Benzyl-5H-1,3,2-oxathi(SIV)azol-5-one (Formula (I), $R^1$=benzyl)

This compound is prepared by the same procedure of Example 3 except that an equivalent amount of 3-phenylpropionic acid ethyl ester, the compound of formula (II) where $R^1$ benzyl and $R^2$ is ethyl, is used in place of the compound of formula (III) where $R^1$ is 4-methoxphenyl and $R^2$ is CH$_2$CH$_2$SiMe$_3$ in part (B).

EXAMPLE 10

4-(4-Aminophenyl)-5H-1,3,2-oxathi(SIV)azol-5-one (Formula (I), $R^1$=4-aminophenyl)

This compound is prepared by treating 4-(4-nitrophenyl)-5H-1,3,2-oxathi(SIV)azol-5-one from Example 5 with a molar equivalent amount of hydrazine hydrate in ethanol at room temperature in the presence of a catalytic amount of 5-20% palladium on carbon.

EXAMPLE 11

4-(3-Bromophenyl)-5H-1,3,2-oxathi(SIV)azol-5-one (Formula (I), $R^1$=3-bromophenyl)

This compound is prepared by the same procedure of Example 3 except that an equivalent amount of 3-bromophenylacetic acid ethyl ester, the compound of formula (II) where $R^1$ is 3-bromophenyl and $R^1$, is ethyl, is used in place of the compound of formula (III) where $R^1$ is 4-methoxyphenyl and $R^2$ is CH$_2$CH$_2$SiMe$_3$ in part (B).

EXAMPLE 12

4-(Trifluoromethyl)-5H-1,3,2-oxathi(SIV)azol-5-one (Formula (I), $R^1$=trifluoromethyl)

This compound is prepared by the same procedure of Example 3 except that an equivalent amount of 3,3,3-trifluoropropionic acid ethyl ester, the compound of formula (II) where $R^1$ is trifluoromethyl and $R^1$ is ethyl, is used in place of the compound of formula (III) where $R^1$ is 4-methoxyphenyl and $R^2$ is CH$_2$CH$_2$SiMe$_3$ in part (B).

We claim:

1. A compound of formula (I)

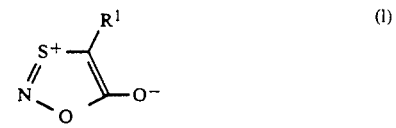

wherein $R^1$ is $C_{1-8}$ alkyl, $C_{2-8}$ alkenyl, $C_{5-8}$ cycloalkyl, aryl-$C_{1-4}$alkyl, heteroaryl or aryl or heteroaryl which is mono-, di-, or trisubstituted independently with halogen, nitro, $C_{2-4}$ alkyl, $C_{1-4}$ alkoxy, trifluoromethyl, amino or $C_{1-4}$ alkyl mono or disubstituted amino with the proviso that $R^1$ can not be 4-bromophenyl or 2,3,4-trimethoxyphenyl, wherein said aryl is phenyl or naphthyl and said heteroaryl is a 5, 6 or 7 member heteroaryl ring interrupted by one or more N, S or O hetero atoms.

2. A compound of claim 1 wherein $R^1$ is phenyl substituted with a halogen, nitro, $C_{2-4}$ alkyl or $C_{1-4}$ alkoxy group.

3. A compound of claim 1 selected from the group:
   4-(4-methoxyphenyl)-5H-1,3,2-oxathi(SIV)azol-5-one
   4-(4-nitrophenyl)-5H-1,3,2-oxathi(SIV)azol-5-one, and
   4-methyl-5H-1,3,2-oxathi(SIV)azol-5-one.

4. A method of treating a cardiovascular disorder by inducing vasodilation in a mammal suffering from said disorder comprising administration of an effective vasodilating amount of a compound of formula (I)

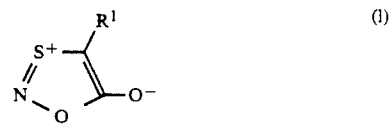

wherein $R^1$ is $C_{1-8}$ alkyl, $C_{2-8}$ alkenyl, $C_{5-8}$ cycloalkyl, aryl-$C_{1-4}$alkyl, aryl or heteroaryl; or aryl or heteroaryl which is mono-, di-, or trisubstituted independently with halogen, nitro, $C_{1-4}$ alkyl, $C_{1-4}$ alkoxy, trifluoromethyl, amino or $C_{1-4}$ alkyl mono or disubstituted amino, wherein said aryl is phenyl or naphthyl and said heteroaryl is a 5, 6 or 7 member heteroaryl ring interrupted by one or more N, S or O hetero atoms.

5. A method of claim 4 wherein the cardiovascular disorder is angina pectoris.

6. A method of claim 4 wherein the cardiovascular disorder is congestive heart failure.

7. A method of claim 4 wherein the cardiovascular disorder is myocardial ischemia.

8. A pharmaceutical formulation comprising an effective vasodilating amount of a compound of formula (I)

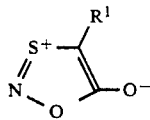 (I)

wherein $R^1$ is $C_{1-8}$ alkyl, $C_{2-8}$ alkenyl, $C_{5-8}$ cycloalkyl, aryl-$C_{1-4}$ alkyl, aryl or heteroaryl; or aryl or heteroaryl which is mono-, di-, or trisubstituted independently with halogen, nitro, $C_{1-4}$ alkyl, $C_{1-4}$ alkoxy, trifluoromethyl, amino or $C_{1-4}$ alkyl mono is disubstituted amino and a pharmaceutically acceptable carrier, wherein said aryl is phenyl or naphthyl and said heteroaryl is a 5, 6 or 7 member heteroaryl ring interrupted by one or more N, S or O hetero atoms.

9. A formulation of claim 8 in the unit dose form of a tablet.

10. A formulation of claim 8 in the form of a transdermal system.

11. A formulation of claim 8 in the form of a sublingual aerosol.

12. A formulation of claim 8 in the unit dose form of a suppository.

* * * * *